United States Patent
Anapliotis

(10) Patent No.: US 10,722,371 B2
(45) Date of Patent: *Jul. 28, 2020

(54) COUPLING DEVICE FOR CONNECTING PROSTHESIS COMPONENTS BY A SELF-LOCKING PRESS FIT

(71) Applicant: Aristotech Holding GmbH, Berlin (DE)

(72) Inventor: Emmanuel Anapliotis, Berlin (DE)

(73) Assignee: Aristotech Holding GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,037

(22) Filed: May 20, 2019

(65) Prior Publication Data

US 2019/0269515 A1 Sep. 5, 2019

Related U.S. Application Data

(63) Continuation of application No. 15/979,035, filed on May 14, 2018, now Pat. No. 10,350,075.

(30) Foreign Application Priority Data

May 16, 2017 (DE) .......................... 10 2017 004 911

(51) Int. Cl.
*A61F 2/36* (2006.01)
*A61F 2/30* (2006.01)

(52) U.S. Cl.
CPC .... *A61F 2/3609* (2013.01); *A61F 2002/3069* (2013.01); *A61F 2002/30205* (2013.01);
(Continued)

(58) Field of Classification Search
CPC ............... A61F 2/3609; A61F 2/30734; A61F 2002/365; A61F 2002/30217;
(Continued)

(56) References Cited

U.S. PATENT DOCUMENTS

| 5,387,244 A * | 2/1995 | Breard .................. A61F 2/3609 623/23.15 |
| 2002/0193882 A1* | 12/2002 | Koller ................... A61F 2/4684 623/23.12 |

(Continued)

FOREIGN PATENT DOCUMENTS

| CH | 676922 | 3/1991 |
| DE | 4008563 | 9/1990 |

(Continued)

OTHER PUBLICATIONS

Office Action, DE102017994911.4, dated Jan. 26, 2018.

(Continued)

*Primary Examiner* — Brian A Dukert
(74) *Attorney, Agent, or Firm* — Andrus Intellectual Property Law, LLP

(57) ABSTRACT

A coupling device is for connecting prosthesis components by a self-locking press fit on an end, formed as a cone, of a first prosthesis component that is inserted in bone tissue. The coupling device has an outer coupling body with a socket having a conically tapering inner wall, and an expansion sleeve having a lateral surface forming a male taper and an operative forming a female tape. The expansion sleeve is mounted in the socket so as to be rotatable about the longitudinal axis thereof, and receives the cone. The expansion sleeve is expandable radially outwardly to form the self-locking press fit, such that the expansion sleeve widens radially when the cone is inserted into the expansion sleeve. As a result, the self-locking press fit between the cone of the first prosthesis component and the coupling device is established.

20 Claims, 8 Drawing Sheets

(52) U.S. Cl.
CPC .............. *A61F 2002/30332* (2013.01); *A61F 2002/30428* (2013.01); *A61F 2002/30474* (2013.01); *A61F 2002/30594* (2013.01); *A61F 2002/365* (2013.01); *A61F 2002/3625* (2013.01); *A61F 2002/3654* (2013.01); *A61F 2002/3674* (2013.01)

(58) Field of Classification Search
CPC .. A61F 2002/30474; A61F 2002/30345; A61F 2002/4037; A61F 2002/30332; A61F 2002/30594; A61F 2002/3674
See application file for complete search history.

(56) References Cited

U.S. PATENT DOCUMENTS

| | | |
|---|---|---|
| 2006/0188845 A1 | 8/2006 | Serafin et al. |
| 2008/0262626 A1 | 10/2008 | Raugel |
| 2011/0087335 A1 | 4/2011 | Newsome et al. |

FOREIGN PATENT DOCUMENTS

| | | |
|---|---|---|
| DE | 19904437 | 8/2000 |
| DE | 10303660 | 7/2004 |
| EP | 0562782 | 9/1993 |
| EP | 1293179 | 3/2003 |
| EP | 2459124 | 6/2012 |
| EP | 2915506 | 9/2015 |
| WO | WO 2005120596 | 12/2005 |
| WO | WO 2014140639 | 9/2014 |

OTHER PUBLICATIONS

Decision to Grant, DE102017994911.4, dated Feb. 22, 2018.
EP Search Report and Written Opinion, EP Patent Application No. 18172407, dated Sep. 17, 2018.

\* cited by examiner

Neckline Z

Neckline Y

Neckline Y

COUPLING DEVICE FOR CONNECTING PROSTHESIS COMPONENTS BY A SELF-LOCKING PRESS FIT

CROSS-REFERENCE TO RELATED APPLICATIONS

This application is a continuation of U.S. application Ser. No. 15/979,035, filed May 14, 2018, which claims the benefit of and priority from German Patent Application No. 10 201 7 004 911.4, filed May 16, 2017 in the German Patent Office. Both the U.S. and the German applications are incorporated herein by reference, in their entireties.

FIELD

The invention relates to a coupling device, by means of which components of a prosthesis can be clamped against one another by means of a cone connection so as to form a self-locking press fit, and can thus be interconnected. In particular, the invention relates to a coupling device for the cone connection between the hip-stem and the insertion head of a hip endoprosthesis.

BACKGROUND

In particular in the field of hip endoprosthetics, the cone insertion connection between the femoral head and the hip-stem has proven itself as a stable self-locking clamped connection. Moreover, on account of the clamping properties thereof, cone insertion connections are also used in other prosthetics care systems.

However, problems arise in relation to renewing the cone insertion connection when one of the prosthetics components of the prosthetics system needs to be replaced.

For example, replacing the joint head is generally associated with altering the ball socket. In such a case, in order not to have to also explant the existing shaft and replace said shaft with a shaft that corresponds to the cone of the new joint head, adapter sleeves have been developed, by means of which the new joint head can be securely connected, in situ, with the remaining shaft, by means of a cone insertion connection.

A plurality of conical adapter sleeves is known from the prior art, which sleeves have been designed for various purposes.

DE 40 08 563 A1 discloses a cone insertion connection of this kind, in which a conical adapter is used as a coupling means between the joint head and the shaft neck in order to be able to connect joint heads and shaft necks by means of a frictional connection, it being possible for the joint and the shaft neck to be produced from different materials and to also have different conicities.

Pre-assembled adapters for cone insertion connections are known from CH 676 922 A5 and WO 2005/012596 A1. Said latter document in addition discloses the production of a conical adapter of this kind from biocompatible plastics materials.

It is also known that, after the joint head has been removed, the surface a shaft cone no longer has the quality that allows it to be pushed onto a replacement head in a manner free of stress concentrations. As a result of said stress concentrations, fractures and breaks may occur in the joint head, which can in turn lead to renewed altering of the replacement joint head.

This problem is addressed in DE 103 03 660 B4, which document specifies an adapter for providing existing shafts with new joint heads, which adapter ensures that the stresses are distributed uniformly over the contact surface or are diverted at least into the upper region of the cone. For this purpose, the adapter comprises a groove that extends upwards from the lower, wider face of said adapter, and the female taper of said adapter has a curved course.

DE 199 04 437 A1 describes a conical adapter that has particular elasticity and damping properties. In order to more uniformly divert the stress between the cone of the shaft and the ball head, the adapter is formed as a porous package. The disclosed design makes it possible to replace damaged ball heads without it being necessary to remove the shaft, even if the state of the surface of the cone would no longer allow the ball heads to be placed on directly.

In order to compensate for winding errors in the cone on the prosthesis neck while at the same time increasing the useful life of the prosthesis, EP 2 459 124 B4 provides an adapter that, although fundamentally a conical molded body, nonetheless comprises resilient and bearing portions which divert the force into a defined region in the joint head and thus relieve the load-bearing regions.

A problem in prostheses that bear a cone is that the cone geometries are not standardized, and therefore the dimensions of the cones of different manufacturers may differ significantly from one another. Specifications such as "12/14 Euro cone" or "12/14 standard cone" likewise do not denote a cone geometry that is subject to a standard and which guarantees standardized dimensions irrespective of the manufacturer.

If the cone of the prosthesis is then additionally damaged or if the tolerances thereof are outside the standard deviation usual in production, it is no longer possible to ensure a secure and long-term stable cone insertion connection between the prosthesis components, even when using a cone adapter.

SUMMARY

The object of the invention is therefore that of specifying an adapter system for a cone insertion connection between prosthesis components, which system produces a long-time stable and secure press fit between the prosthesis components, even in the case of damaged cones or cones of which the geometries are unknown or cannot be determined.

In order to achieve this object, a coupling device for connecting prosthesis components is specified, by means of which device it is possible to produce a self-locking press fit on an end, formed as a cone, of a first prosthesis component that is inserted in bone tissue, and which device comprises an outer coupling body having at least one socket that has a conically tapering inner wall, and an expansion sleeve having a lateral surface that forms a male taper and an operative surface that forms a female taper.

In this case, the expansion sleeve is mounted in the socket in the coupling body so as to be rotatable about the longitudinal axis thereof, and is designed for receiving the cone of the first prosthesis component.

The coupling system is characterized in that the expansion sleeve is designed so as to be expandable radially outwardly in order to form the self-locking press fit, such that the expansion sleeve widens radially when the cone of the first prosthesis component is inserted into the expansion sleeve, as a result of which widening the self-locking press fit between the cone of the first prosthesis component and the coupling device can be established.

When forming the self-locking press fit, a plurality of pairs of surfaces interact with one another in the coupling device according to the invention.

In this case, the following pairs of surfaces are at least involved in forming the press fit between the first prosthesis component and the coupling device:

a) the cone surface of the first prosthesis component and the operative surface of the female taper of the expansion sleeve, and b) the lateral surface of the expansion sleeve and the inner wall of the socket.

In the case of coupling to a second prosthesis component, at least the following pair of surfaces is additionally involved in a clamped connection:

c) the outer surface of the conical outer contour of the coupling body, and the inner surface of a conical inner contour in a second prosthesis component.

Said latter embodiment relates in particular to a conical adapter that is inserted between a joint heat and a shaft neck in a hip endoprosthesis, in order to fix the joint head on the shaft cone.

Further fields of application of a coupling device according to the invention relates to connection elements that are designed to connect prosthesis components such as bone nails to one another or to shafts of joint prostheses.

In the design according to the invention, the structural proportions of the expansion sleeve relative to the socket are such that, when not clamped by the cone of the first prosthesis component (free state) the expansion sleeve can rotate freely in the socket. For this purpose, the male taper of the expansion sleeve is advantageously slightly smaller than the internal taper of the socket, such that there is clearance between the expansion sleeve and the socket.

Only when the cone of the first prosthesis component is inserted into the female taper of the expansion sleeve does the expansion sleeve widen, as a result of which the sleeve is expanded and the lateral surface thereof is pressed against the inner wall of the socket, and thus a selflocking press fit is formed.

A first prosthesis component is in particular a hip shaft or an intramedullary bone nail that comprises one or more conical connection regions.

The advantage of the coupling device according to the invention compared with the prior art is that the coupling device can bridge flaws, deformations or tolerance deviations in cones, and can thus connect said cones to replacement components, and therefore the prosthesis components that are still securely located in the bone—and when deemed so by doctors—can be left in situ. As a result, it is possible to avoid complete replacements, which is beneficial to the patient, and the stress caused by a more complex operation is reduced, which in turn reduces the recovery times and improves the recovery prospects.

It has also been found that, when using a coupling device according to the invention, less force needs to be applied when joining the prosthesis components in order to achieve a long-time stable self-locking clamping effect between the prosthesis components.

In order to achieve the radial expandability required for the expansion sleeve to be widenable, the expansion sleeve preferably comprises at least one slit that begins at an edge and extends in the longitudinal direction of the expansion sleeve. In a particular embodiment, the expansion sleeve has a continuous slot in the longitudinal direction, and therefore the expansion sleeve is formed as a split ring.

In order to achieve more uniform force distribution when forming the press fit, in a further embodiment, slots that extend in the longitudinal direction are formed peripherally in the expansion sleeve, which slots advantageously begin alternately at the edge of the wider end and at the edge of the narrower end, such that the expansion sleeve has a serpentine structure.

In order to increase the strength of the press fit, the conicity of the female taper of the expansion sleeve may be slightly smaller than the conicity of the cone of the first prosthesis component, as a result of which the expansion sleeve is forcibly widened when the cone is inserted.

In a further embodiment, the expansion sleeve is pre-assembled in the socket of the coupling body, and is secured, in the axial direction, from slipping out of the socket.

In a first alternative, a radially peripheral bead is formed on the lateral surface of the expansion sleeve in order to hold the expansion sleeve in the socket, which bead can be brought into engagement with a radially peripheral groove in the inner wall of the socket. The groove-bead engagement is designed such that the bead snaps into the groove when the expansion sleeve is inserted, but without the socket clamping the expansion sleeve, i.e. the groove-bead engagement maintains the rotatability of the expansion sleeve about the longitudinal axis thereof.

In a second alternative, the expansion sleeve is held in the socket by means of a radially peripheral undercut being formed in the receiving opening of the socket, on which undercut the lower edge of the expansion sleeve, inserted into the socket on the inside of the socket, is supported. What is essential is that the undercut opening should be larger than the opening of the expansion sleeve female taper located in this region, and that the undercut should surround the expansion sleeve only in the outer edge region thereof. The inner edge region of the expansion sleeve therefore projects over the edge of the undercut, and therefore the undercut does not impede the insertion of the cone of the first prosthesis component into the female taper of the expansion sleeve.

A step-like and radially peripheral constriction is advantageously formed on the inner wall, in the head region of the socket opposite the receiving opening, by means of which constriction the inserted expansion sleeve is held so as to be spaced apart from the head region of the socket. A hole that is open to the surroundings is advantageously formed in the head region of the socket, through which hole air can escape when the cone of the first prosthesis component is introduced. In addition, a corresponding instrument can also be inserted via the hole, by means of which instrument the coupling body can be pushed away from one of the prosthesis components.

In a first embodiment, the coupling body has a conical outer contour which can be brought into a self-locking press fit with a conical inner contour in a second prosthesis component. The external shape and the purpose of said embodiment substantially corresponds to the known conical adapters that are used to establish a self-locking press fit between a joint head and a shaft cone. In this embodiment, the joint head is thus the second prosthesis component.

In a second embodiment, the coupling device comprises a cylindrical coupling body, on each of the ends of which a socket comprising an expansion sleeve mounted therein is formed. A coupling device of this kind is suitable for clamping the conical end regions of two prosthesis components together in a self-locking manner. By way of example, a coupling device of this kind is used in intramedullary elongation of existing hip shafts in the dorsal direction, using bone nails.

The cylindrical coupling body may be straight or curved or angled. Said latter designs are suitable for bridging the joint region in the angled position when permanent or temporally limited arthrodesis is required.

The invention will be explained in greater detail in the following with reference to a plurality of embodiments.

DETAILED DESCRIPTION

Figure 1:
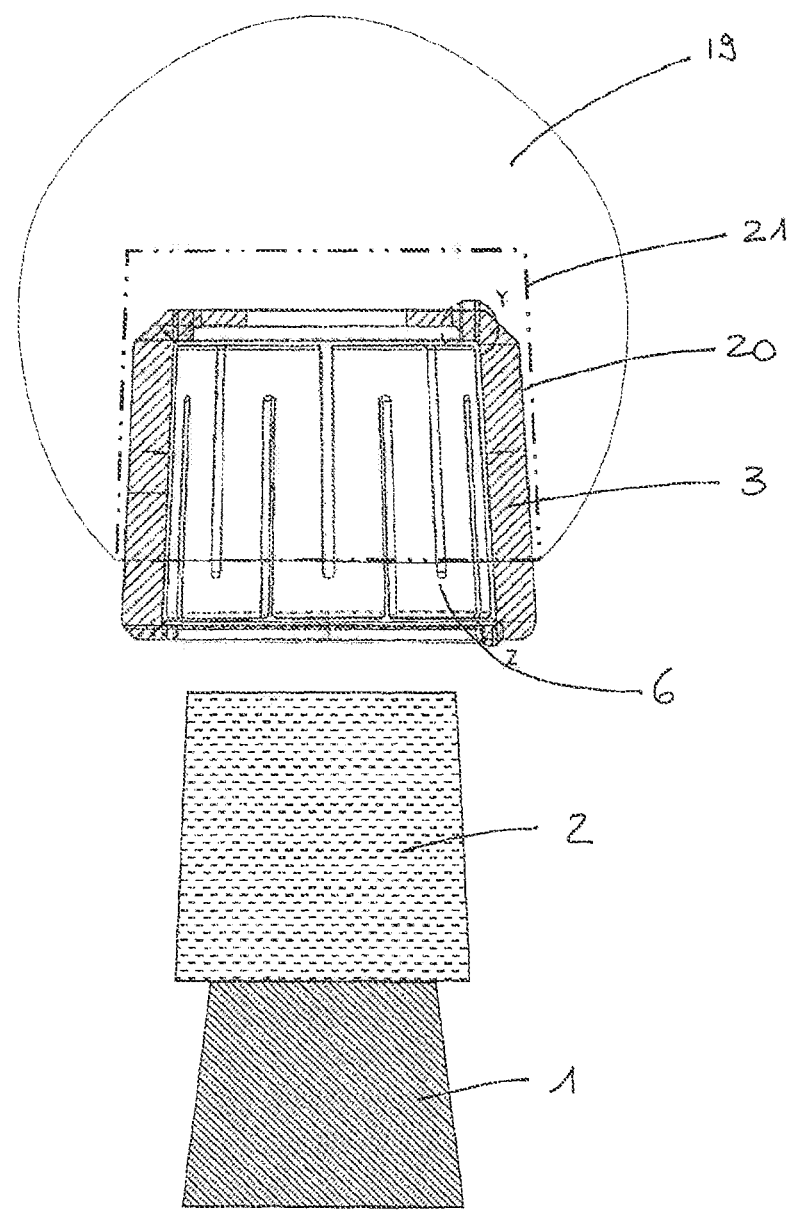
FIG. 1: shows a structure, by way of example, of a connection between of prosthesis components, in which a first and a second prosthesis component are interconnected by means of a coupling device according to the invention.

FIG. 1 shows a structure, by way of example, of a prosthesis in which a first prosthesis component 1 having a conical connection region 2, and a second prosthesis component 19 having a conical female taper 21 are coupled together by means of two self-locking press fits. The connection between the prosthesis components 1 and 2 is established by a coupling device according to the invention that is assembled from an outer coupling body 3 having a conical outer contour 20 and an expansion sleeve 6 that is formed in a socket 4 and is slotted.

The conical expansion sleeve 6 is rotatably mounted in the conical socket 4 of the coupling body 3 and is secured, by means of the undercut 17, from slipping out of the socket 4.

In order to produce the press fit between the first prosthesis component 1 and the coupling device, the cone 2 of the first prosthesis component 1 is pushed into the female taper 9 of the expansion sleeve 6, as a result of which the expansion sleeve 6 is widened and the lateral surface 8 thereof is pressed against the inner wall 5 of the socket 4, with the result that the cone 2 of the first prosthesis component 1 and the coupling body 3 are clamped together.

The second press fit is formed when the second prosthesis component 19 is placed onto the conical outer contour 20 of the coupling body 3, by means of the conical coupling body 3 being driven into a conical receptacle 21 of the second prosthesis component 19.

In FIG. 1, by way of example a cone 2 of a hip shaft is shown as the first prosthesis component 1 and the joint head to be pushed onto the cone 21 of the hip shaft is shown as the second prosthesis component 19 of the prosthesis.

Figure 2A:
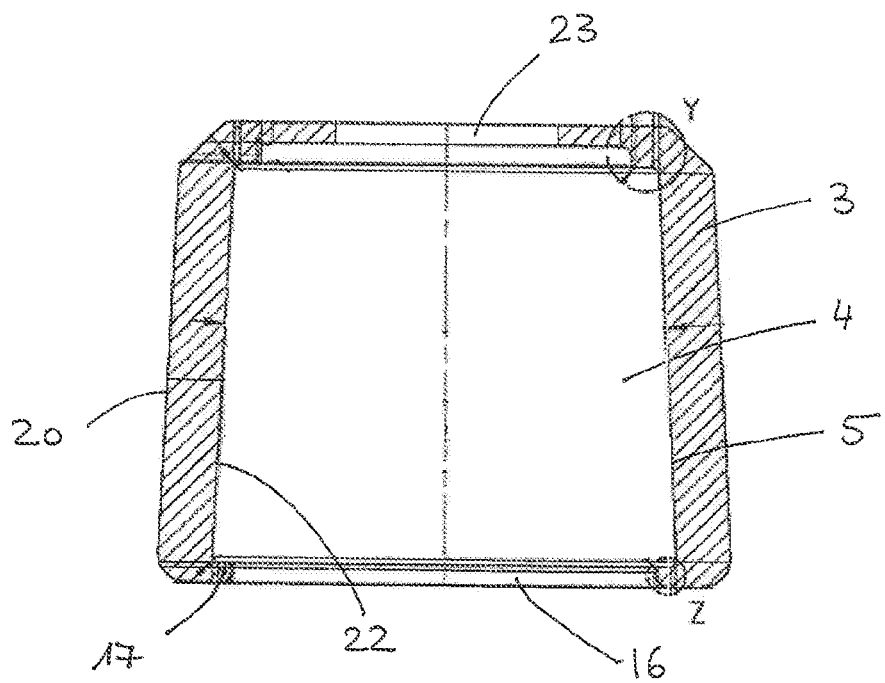
FIG. 2a-c: show a first variant of an outer coupling body.
Figure 2B:
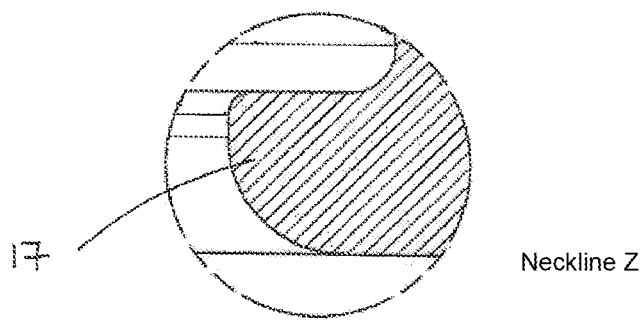
Figure 2C:
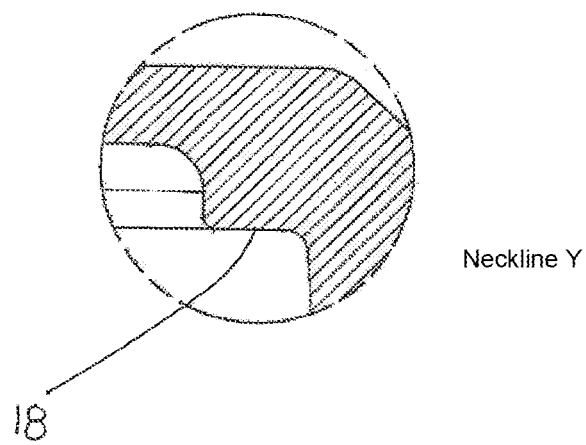

FIG. 2a-c show a first embodiment of an outer coupling body 3. The external shape 20 of the coupling body 3 shown is conical and the outer contour of said body thus corresponds to the adapters that are known in hip endoprosthesis and are used to connect ball heads and hip shafts. The socket 4 formed in the interior of the adapter is also conical. In the case shown, the cone angle of the male taper contour 20 and of the internal taper 22 are identical. The sizes of the cone angles may, however, also be different from one another.

The receiving opening 16 of the socket 4, in which opening a peripheral undercut 17 is formed, as a result of which undercut the receiving opening 16 has a cross-section that is narrowed relative to the adjacent region of the socket 4, is located in the region of the wide end of the coupling body 3. The undercut 17 is shown again in detail in FIG. 2b.

A step-like and radially peripheral constriction 18 (FIG. 2c) is formed in the head region of the socket 4, by means of which constriction the expansion sleeve (not shown) is held so as to be spaced apart from the head region of the socket 4. The hole 23 that is additionally located in the head region of the socket 4 has a plurality of functions. Firstly, said hole allows air to escape when the cone of the first prosthesis component is inserted, and additionally a corresponding instrument can be inserted via the hole 23, by means of which instrument the coupling body 3 can be pushed away from one of the prosthesis components.

Figure 3A:
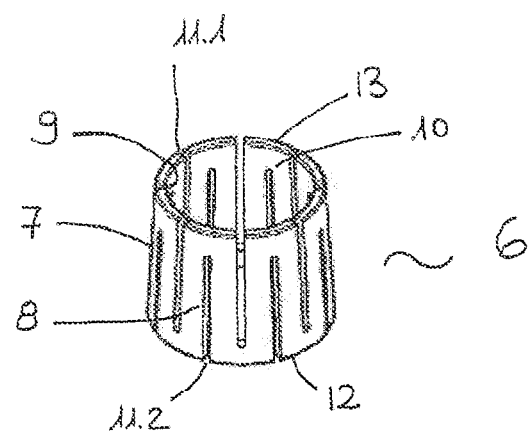
FIG. 3a-b: show a first variant of an expansion sleeve.
Figure 3B:
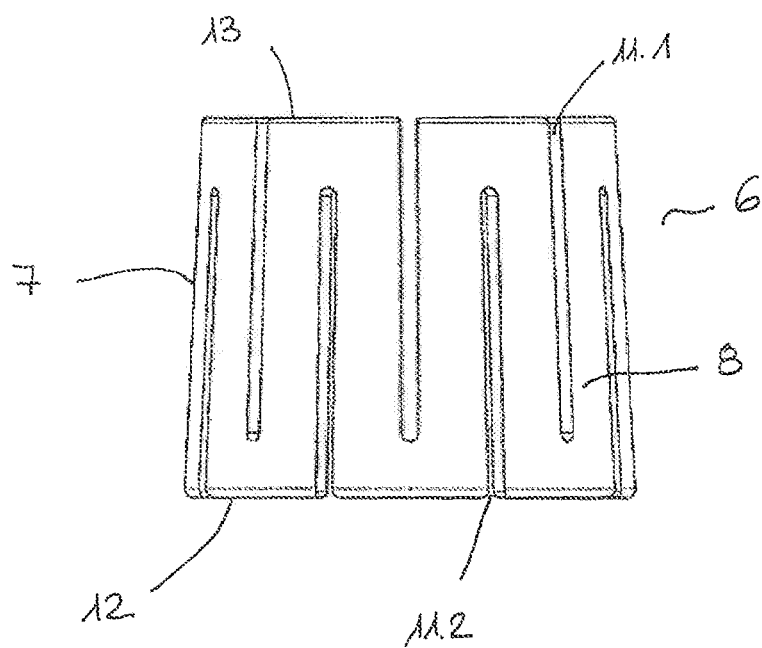

FIGS. 3a and b show an expansion sleeve 6 that is compatible with the coupling body 3 shown in FIG. 2a-c.

The expansion sleeve 6 shown has a male taper 7 having a lateral surface 8 and a female taper 9 having an operative surface 10. In order to produce radial expandability, the expansion sleeve 6 is slotted in the longitudinal direction, slots 11.1, 11.2 extending in the longitudinal direction being formed peripherally in the expansion sleeve 6, which slots begin alternately at the edge 12 of the wider end and at the edge 13 of the narrower end, such that the expansion sleeve 6 has a serpentine structure.

Figure 4:
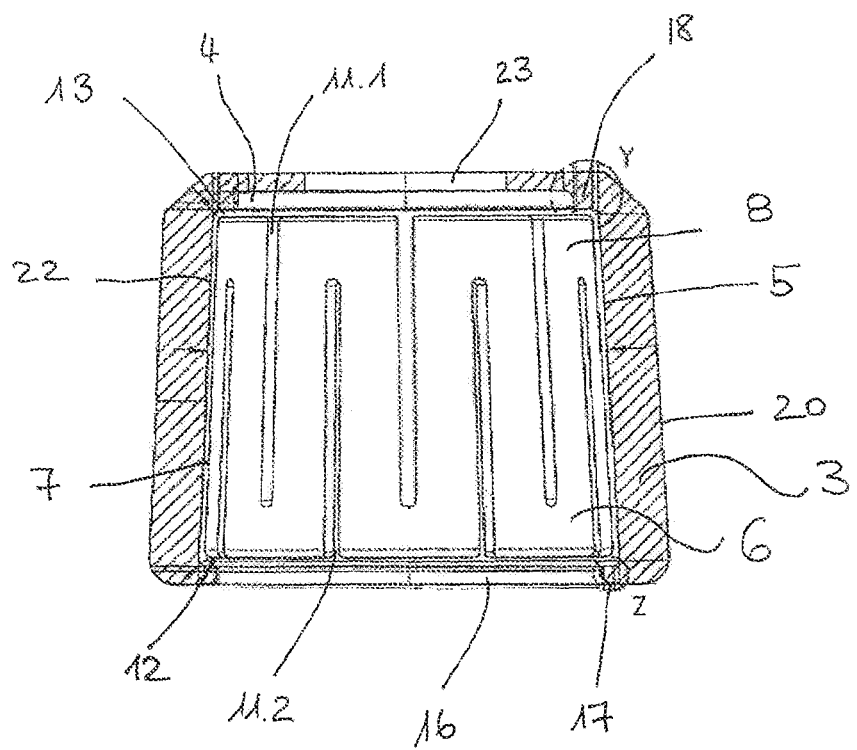
FIG. 4: shows a first variant of a coupling device assembled from an expansion sleeve and a coupling body.

FIG. 4 shows an alternative of a coupling device, in which an expansion sleeve 6, as shown in FIGS. 3a and b, is inserted into the socket 4 of a coupling body 3 in an embodiment according to FIG. 2a-c.

As a result of clearance being created between the lateral surface 8 of the male taper 7 and the inner wall 5 of the coupling body 3, the expansion sleeve 6 is rotatably mounted in the socket 4 and secured, by the undercut 17, from slipping out of the socket 4, the lower edge 12 of the expansion sleeve 6 being supported on the undercut 17 on the inside of the socket.

What is essential in this embodiment is that the undercut opening should be larger than the in large cone opening of the female taper 9 of the expansion sleeve 6, such that the undercut 17 surrounds the expansion sleeve 6 only in the outer edge region 12 thereof. The inner edge region 12 of the expansion sleeve 6 therefore projects over the edge of the undercut 17 in the direction of the longitudinal axis of the coupling device, and therefore the undercut 17 does not impede the insertion of a cone 2 of the first prosthesis component 2 (not shown) into the female taper 9 of the expansion sleeve 6.

At the head end of the socket 4, the constriction 18 prevents the upper edge 13 of the expansion sleeve 6 from striking the end region of the coupling body 3.

Figure 5A:
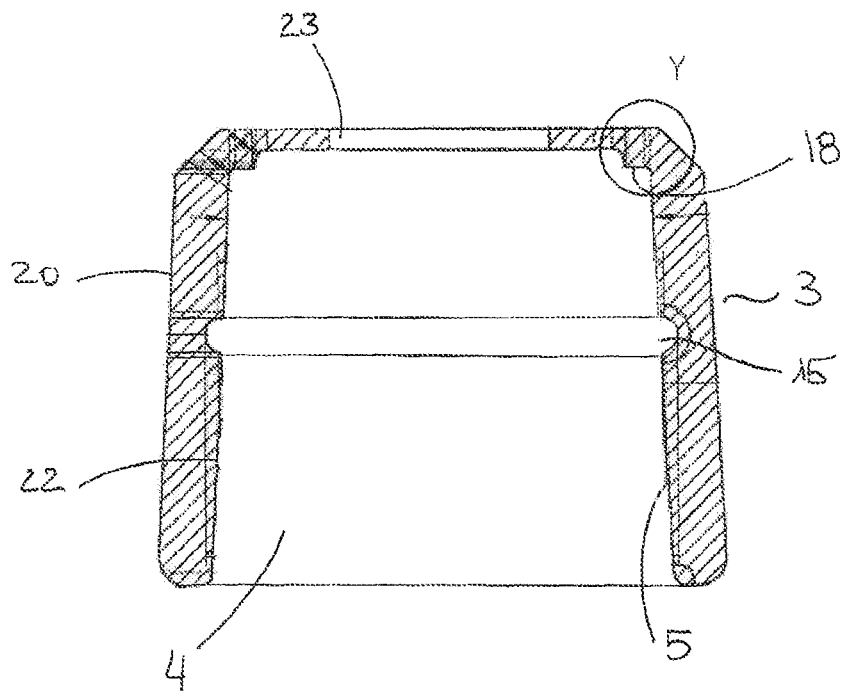
FIG. 5a-b: show a second variant of an outer coupling body.
Figure 5B:
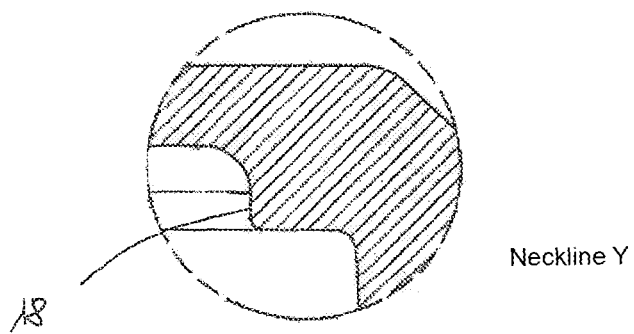

FIGS. 5a and 5b show a second embodiment of an outer coupling body 3. The external shape 20 of the coupling body 3 shown is likewise conical and, in this variant too, the outer contour of said body corresponds to the adapters that are known in hip endoprosthesis and are used to connect ball heads and hip shafts.

The socket 4 formed in the interior of the adapter-like coupling body 3 is also conical. In the case shown, as in the variant described above, the cone angle of the male taper contour 20 and of the internal taper 22 are identical. The sizes of the cone angles may, however, also be different from one another in this embodiment too.

A radially peripheral groove 15 is formed in the inner wall 5 of the socket 4, which groove can be brought into engagement with a radial bead 14 on the lateral surface 8 of an expansion sleeve 6.

A step-like and radially peripheral construction 18 (FIG. 5b) is again formed in the head region of the socket 4, by means of which constriction the expansion sleeve (not shown) is held so as to be spaced apart from the head region of the socket 4. In this case, too, the hole 23 that is additionally located in the head region of the socket 4 has the functions of allowing air to escape when the cone of the first prosthesis component is inserted, or of allowing a corresponding instrument to be inserted via the hole 23 in order to push the coupling body 3 away from one of the prosthesis components 1 and/or 19.

Figure 6A:
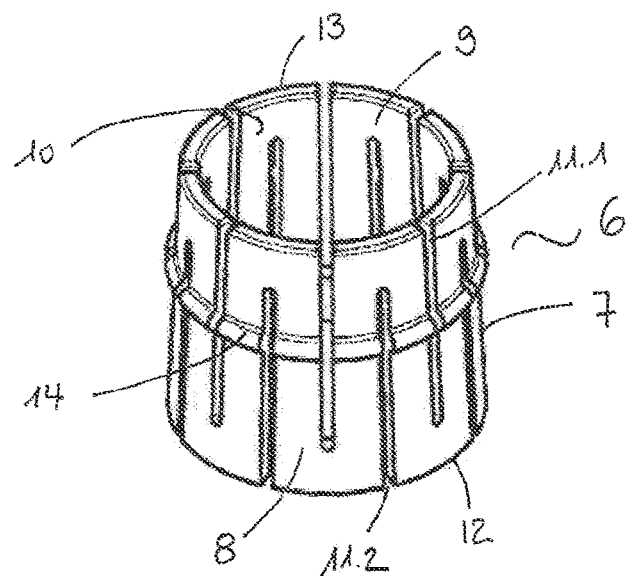
FIG. 6a-c: show a second variant of an expansion sleeve.
Figure 6B:
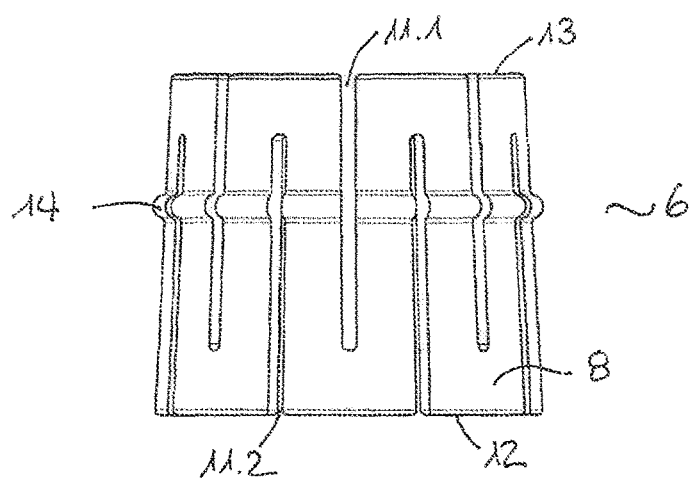
Figure 6C:
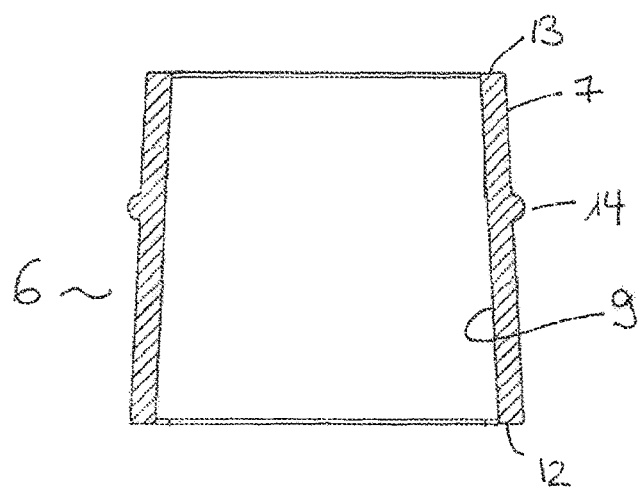

FIG. 6a-c show a conical expansion sleeve 6 that is compatible with a coupling body 3 according to the embodiment shown in FIGS. 5a and b.

The expansion sleeve 6 shown has a male taper 7 comprising a lateral surface 8, and a female taper 9 comprising an operative surface 10, the cone angles of the male and female tapers being the same.

A radially peripheral bead 14 is formed on the lateral surface 8 of the expansion sleeve 6, which bead can be brought into engagement with the radially peripheral groove 15 formed in the inner wall 5, in order to hold the expansion sleeve 6 in the socket 4 of the coupling body 3.

In order to be able to widen the expansion sleeve 6 in the radial direction, said sleeve is slotted peripherally, in the longitudinal direction, the slots 11.1 and 11.2 that extend in the longitudinal direction beginning alternately at the edge 12 of the wider end and at the edge 13 of the narrower end of the expansion sleeve 6, such that said sleeve has a serpentine structure that is expandable. In this case, the slots 11.1 and 11.2 divide the radial bead 14 into portions in each case.

Figure 7:
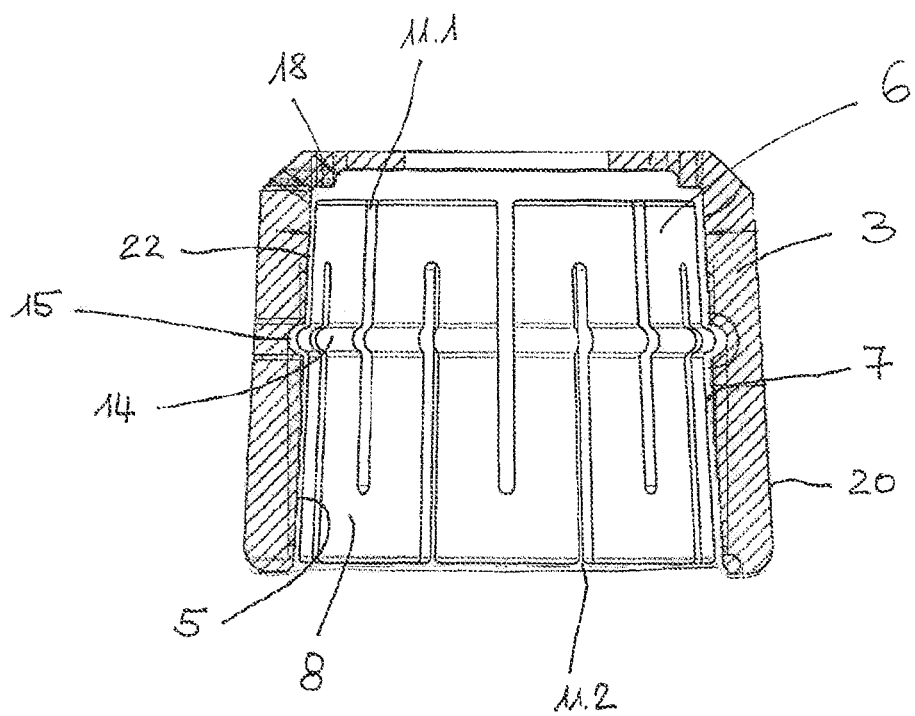
FIG. 7: shows a second variant of a coupling device assembled from an expansion sleeve and a coupling body.

FIG. 7 shows the second alternative of a coupling device, in which the expansion sleeve 6 according to FIG. 6a-c is inserted in the socket 4 of a coupling body 3 as shown by way of example in FIG. 5a-b. The expansion sleeve 6 is movably mounted in the socket 4 and secured from slipping out of the socket 4 by means of the bead 14 engaging in the groove 15.

Figure 8:
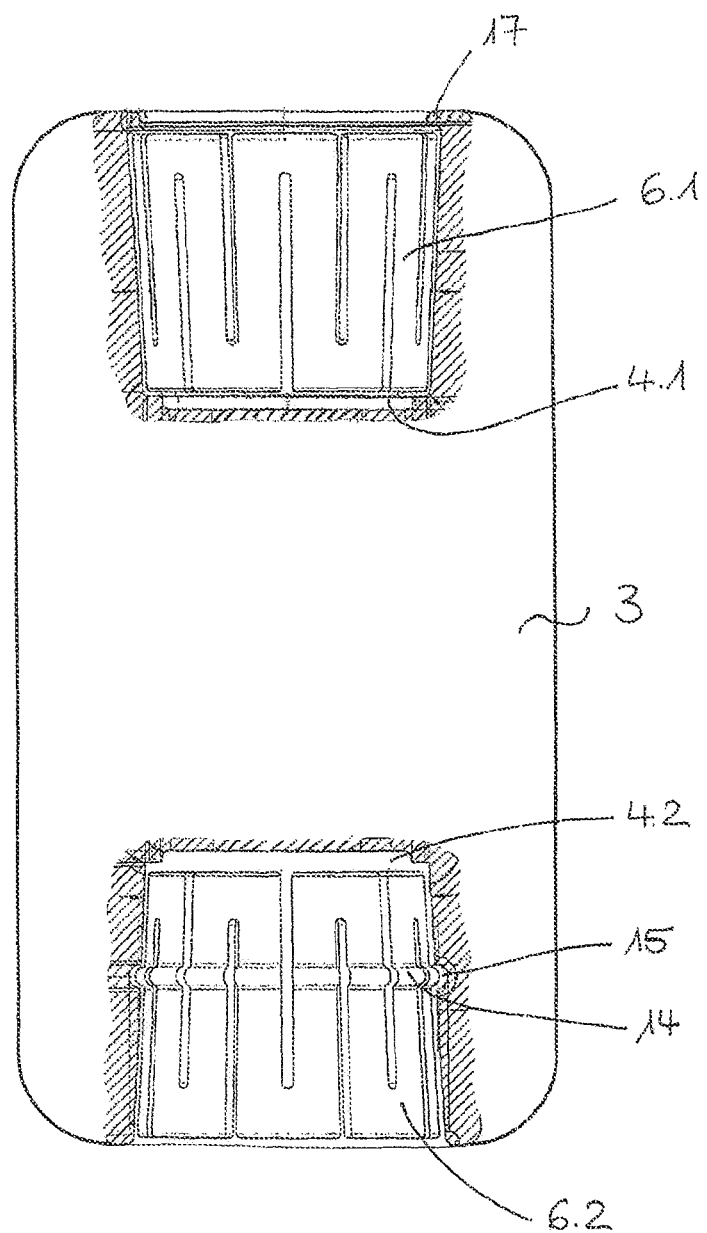
FIG. 8: shows an alternative embodiment of a coupling device comprising two expansion sleeve inserts formed at the opposing ends of the coupling device.

FIG. 8 shows an embodiment of a coupling device according to the invention, which device can be used for coupling two prosthesis components that each have at least one conical end region.

Prosthesis components of this kind are in particular bone nails and shafts of joint prostheses, and therefore a coupling device of this kind can be used to elongate existing shafts in the dorsal direction for example.

In order to elongate the shaft end of a hip shaft in the region of the femur, the coupling device having the expansion sleeve mounted in the proximal socket is pushed onto the cone on the shaft end for example. In order to be connected to an intramedullary bone nail, the expansion sleeve mounted in the dorsally formed socket is pushed onto the cone of the bone nail, as a result of which the hip shaft and the bone nail are each coupled together, on either side, in the longitudinal direction, by means of a self-locking press fit.

For this purpose, the coupling device shown in FIG. 8 comprises a cylindrical coupling body 3 which is straight in this embodiment and on each of the opposing ends of which a socket 4.1 and 4.2, respectively, comprising an expansion sleeve 6.1 and 6.2, respectively, mounted therein is formed.

The combination of the expansion sleeve 6.1 and the socket 4.1 which is formed on the upper end of the coupling body 3 corresponds to an embodiment as described with reference to FIG. 4. The combination of the expansion sleeve 6.2 and the socket 4.2 located on the opposing end of the coupling body 3 is a variant according to the description of FIG. 7.

LIST OF REFERENCE SIGNS 1 first prosthesis component
2 cone of the first prosthesis component
3 outer coupling body
4 socket
5 inner wall of the socket
6 expansion sleeve
7 male taper
8 lateral surface
9 female taper
10 operative surface
11 slot
12 edge at the wide cone end of the expansion sleeve
13 edge at the narrow cone end of the expansion sleeve
14 bead on the lateral surface of the expansion sleeve
15 groove in the inner wall of the socket
16 receiving opening
17 radially peripheral undercut
18 step-like and radially peripheral constriction
19 second prosthesis component
20 conical outer contour of the coupling device
21 conical inner contour in a second prosthesis component
22 internal taper (female taper of the socket)
23 hole, open to the surroundings, in the head region of the socket

What is claimed is:

1. A device for coupling a first prosthesis component to a second prosthesis component, the device comprising:
    an outer coupling body having a socket and a conical outer surface configured to contact and couple to the second prosthesis component; and
    an expansion sleeve disposed in the socket and configured to radially outwardly expand as the first prosthesis component is received into the expansion sleeve within the socket.

2. The device according to claim 1, wherein the outer coupling body is configured to be inserted into the second prosthesis component.

3. The device according to claim 1, wherein the socket has an inner wall against which the expansion sleeve presses as the expansion sleeve radially outwardly expands.

4. The device according to claim 3, wherein the expansion sleeve is axially retained in the socket and rotatable therein about a longitudinal axis along which the socket extends.

5. The device according to claim 4, wherein the outer coupling body has an undercut radially inwardly extending into the socket to axially retain the expansion sleeve in the socket.

6. The device according to claim 4, wherein the expansion sleeve is tapered and has a narrow end and an opposite, wider end.

7. The device according to claim 6, wherein the narrow end has an edge and the wider end has an edge, and wherein the expansion sleeve has a first plurality of slots that extend from the edge of the narrow end toward the wider end and a second plurality of slots that extend from the edge of the wider end toward the narrow end.

8. The device according to claim 7, wherein the first plurality of slots is interdigitated with the second plurality of slots.

9. The device according to claim 8, wherein the expansion sleeve has a serpentine structure.

10. The device according to claim 6, wherein the narrow end and the wider end both radially outwardly expand as the first prosthesis component is received into the expansion sleeve.

11. A device for coupling prosthesis components, the device comprising:
    an outer coupling body having a socket; and
    an expansion sleeve axially retained in the socket and rotatable therein about a longitudinal axis along which the socket extends;
    wherein the expansion sleeve is configured to radially outwardly expand as a first prosthesis component is received into the expansion sleeve within the socket;
    wherein the expansion sleeve has a first end and a second end, both of which are received within the socket.

12. The device of claim 11, wherein the first and second ends of the expansion sleeve both radially outwardly expand as the first prosthesis component is received into the expansion sleeve.

13. The device of claim 11, wherein the first end has an edge and the second end has an edge, and wherein the expansion sleeve has a first plurality of slots that extend from the edge of the first end toward the second end and a second plurality of slots that extend from the edge of the second end toward the first end.

14. The device according to claim 13, wherein the first plurality of slots is interdigitated with the second plurality of slots.

15. The device of claim 11, wherein the outer coupling body has an outer surface configured to contact and couple to a second prosthesis component.

16. The device of claim 11, wherein the expansion sleeve has a conical outer surface and the socket has a conical inner wall.

17. The device of claim 11, wherein the expansion sleeve has an outer surface with a bead radially outwardly extending therefrom, and the socket has an inner wall with a peripheral groove that engages the bead to axially retain the expansion sleeve in the socket.

18. The device according to claim 11, wherein the outer coupling body has an undercut radially inwardly extending into the socket to axially retain the expansion sleeve in the socket.

19. The device according to claim 11, wherein when the first prosthesis component is not received in the expansion sleeve, a clearance exists between an outer surface of the expansion sleeve and an inner wall of the socket.

20. A device for coupling a first prosthesis component to a second prosthesis component, the device comprising:
    an outer coupling body having a socket and an outer surface configured to contact and couple to the second prosthesis component; and
    an expansion sleeve disposed in the socket and configured to radially outwardly expand as the first prosthesis component is received into the expansion sleeve within the socket;
    wherein the socket has an inner wall against which the expansion sleeve presses as the expansion sleeve radially outwardly expands;
    wherein the expansion sleeve is axially retained in the socket and rotatable therein about a longitudinal axis along which the socket extends; and
    wherein the expansion sleeve is tapered and has a narrow end and an opposite, wider end, and the narrow end and the wider end both radially outwardly expand as the first prosthesis component is received into the expansion sleeve.

* * * * *